United States Patent
Sharma et al.

(10) Patent No.: US 11,103,145 B1
(45) Date of Patent: Aug. 31, 2021

(54) PHYSIOLOGICAL SIGNAL MONITORING AND APPARATUS THEREFOR

(71) Applicant: VivaQuant LLC, St. Paul, MN (US)

(72) Inventors: Arjun Sharma, St. Paul, MN (US); Marina Brockway, St. Paul, MN (US); Brian Brockway, St. Paul, MN (US)

(73) Assignee: VivaQuant LLC, Saint Paul, MN (US)

( * ) Notice: Subject to any disclaimer, the term of this patent is extended or adjusted under 35 U.S.C. 154(b) by 465 days.

(21) Appl. No.: 16/008,537

(22) Filed: Jun. 14, 2018

Related U.S. Application Data

(60) Provisional application No. 62/519,640, filed on Jun. 14, 2017.

(51) Int. Cl.
*A61B 5/0205* (2006.01)
*A61B 5/1455* (2006.01)
(Continued)

(52) U.S. Cl.
CPC ...... *A61B 5/02055* (2013.01); *A61B 5/14552* (2013.01); *A61B 5/25* (2021.01); *A61B 5/361* (2021.01); *A61B 5/363* (2021.01); *A61B 5/6816* (2013.01); *A61B 5/6817* (2013.01); *A61B 5/6819* (2013.01); *A61B 5/6822* (2013.01); *A61B 5/6823* (2013.01); *A61B 5/6824* (2013.01); *A61B 5/02405* (2013.01); *A61B 5/02427* (2013.01); *A61B 5/0809* (2013.01)

(58) Field of Classification Search
CPC ... A61B 5/02055; A61B 5/0408; A61B 5/046; A61B 5/0464; A61B 5/14552; A61B 5/6816; A61B 5/6817; A61B 5/6819; A61B 5/6822; A61B 5/6823; A61B 5/6824; A61B 5/02405; A61B 5/02427; A61B 5/0809

USPC .......................................................... 600/513
See application file for complete search history.

(56) References Cited

U.S. PATENT DOCUMENTS 5,090,418 A   2/1992   Squires et al.
5,279,283 A   1/1994   Dillon
(Continued)

FOREIGN PATENT DOCUMENTS

JP   2012 045304 A   3/2012
WO   2006/044699 A2   4/2006
(Continued)

OTHER PUBLICATIONS

Widrow, et al., "Adaptive noise cancelling: principles and applications," IEEE Proc., 63(12):1692-1716 (Dec. 1975).
(Continued)

*Primary Examiner* — Aaron F Roane
(74) *Attorney, Agent, or Firm* — Crawford Maunu PLLC

(57) ABSTRACT

Aspects of the present disclosure are directed to apparatuses and methods for monitoring vital signs from a human being. Various such aspects involve an apparatus or method involving the monitoring of vital signs in a manner that facilitates enhanced characterization of physiological conditions. In many embodiments, two or more such vital signs are monitored. A signal acquisition, digitization, and computing module removing noise, extracts information useful for diagnosing a health or fitness characteristic of the human being, and/or compresses information to reduce data volume. A wireless communications circuit transmits the vital signs to a receiver.

20 Claims, 6 Drawing Sheets

(51) Int. Cl.
  *A61B 5/00* (2006.01)
  *A61B 5/25* (2021.01)
  *A61B 5/361* (2021.01)
  *A61B 5/363* (2021.01)
  *A61B 5/08* (2006.01)
  *A61B 5/024* (2006.01)

(56) References Cited

U.S. PATENT DOCUMENTS

| | | |
|---|---|---|
| 5,313,953 A | 5/1994 | Yomtov et al. |
| 5,331,959 A | 7/1994 | Imran |
| 5,521,851 A | 5/1996 | Wei et al. |
| 5,776,073 A | 7/1998 | Garfield et al. |
| 5,792,065 A | 8/1998 | Xue et al. |
| 5,817,027 A | 10/1998 | Arand et al. |
| 5,827,195 A | 10/1998 | Lander |
| 5,987,352 A | 11/1999 | Klein et al. |
| 6,117,077 A | 9/2000 | Del Mar et al. |
| 6,389,308 B1 | 5/2002 | Shusterman |
| 6,589,189 B2 | 7/2003 | Meyerson et al. |
| 6,690,959 B2 | 2/2004 | Thompson |
| 6,701,170 B2 | 3/2004 | Stetson |
| 6,775,571 B1 | 8/2004 | Kroll |
| 6,821,256 B2 | 11/2004 | Ackerman et al. |
| 6,822,564 B2 | 11/2004 | Al-Ali |
| 6,856,832 B1 | 2/2005 | Matsumura et al. |
| 7,096,060 B2 | 8/2006 | Arand et al. |
| 7,099,714 B2 | 8/2006 | Houben |
| 7,115,096 B2 | 10/2006 | Siejko et al. |
| 7,236,819 B2 | 6/2007 | Brockway et al. |
| 7,272,265 B2 | 9/2007 | Kouri et al. |
| 7,376,453 B1 | 5/2008 | Diab et al. |
| 7,395,114 B2 | 7/2008 | Czygan et al. |
| 7,480,529 B2 | 1/2009 | Li |
| 7,602,985 B2 | 10/2009 | Gao et al. |
| 7,627,369 B2 | 12/2009 | Hunt |
| 7,672,717 B1 | 3/2010 | Zikov et al. |
| 7,840,259 B2 | 11/2010 | Xue et al. |
| 7,846,104 B2 | 12/2010 | MacQuarrie et al. |
| 7,966,067 B2 | 6/2011 | Rousso et al. |
| 8,086,304 B2 | 12/2011 | Brockway et al. |
| 8,201,330 B1 | 6/2012 | Rood et al. |
| 8,214,007 B2 | 7/2012 | Baker et al. |
| 8,271,073 B2 | 9/2012 | Zhang et al. |
| 8,348,852 B2 | 1/2013 | Bauer et al. |
| 8,433,395 B1 | 4/2013 | Brockway et al. |
| 8,460,189 B2 | 6/2013 | Libbus et al. |
| 8,478,389 B1 | 7/2013 | Brockway et al. |
| 8,543,195 B1 | 9/2013 | Brockway et al. |
| 8,588,908 B2 | 11/2013 | Moorman et al. |
| 8,608,984 B1 | 12/2013 | Taranekar et al. |
| 8,632,465 B1 | 1/2014 | Brockway |
| 8,755,876 B2 | 6/2014 | Chon et al. |
| 9,037,477 B2 | 5/2015 | Bardy et al. |
| 9,095,266 B1 | 8/2015 | Fu |
| 9,314,181 B2 | 4/2016 | Brockway et al. |
| 9,408,549 B2 | 8/2016 | Brockway et al. |
| 2002/0077536 A1 | 6/2002 | Diab et al. |
| 2003/0185408 A1 | 10/2003 | Causevic et al. |
| 2003/0236447 A1 | 12/2003 | Ritland |
| 2004/0111141 A1 | 6/2004 | Brabec et al. |
| 2004/0138578 A1 | 7/2004 | Pineda et al. |
| 2004/0167417 A1 | 8/2004 | Schulhauser et al. |
| 2005/0010120 A1 | 1/2005 | Jung et al. |
| 2005/0061319 A1* | 3/2005 | Hartley .............. A61B 5/0538 128/204.18 |
| 2005/0075708 A1 | 4/2005 | O'Brien et al. |
| 2005/0203604 A1 | 9/2005 | Brabec et al. |
| 2005/0234361 A1 | 10/2005 | Holland |
| 2005/0265629 A1 | 12/2005 | Fu et al. |
| 2005/0283090 A1 | 12/2005 | Wells |
| 2006/0094992 A1 | 5/2006 | Imboden et al. |
| 2007/0060815 A1 | 3/2007 | Martin et al. |
| 2007/0219453 A1 | 9/2007 | Kremliovsky et al. |
| 2007/0219455 A1 | 9/2007 | Wong et al. |
| 2007/0260151 A1 | 11/2007 | Clifford |
| 2007/0265508 A1 | 11/2007 | Sheikhzadeh-Nadjar |
| 2008/0065158 A1 | 3/2008 | Ben-Ezra et al. |
| 2008/0097280 A1 | 4/2008 | Martin et al. |
| 2008/0097537 A1 | 4/2008 | Duann et al. |
| 2008/0183093 A1 | 7/2008 | Duann et al. |
| 2008/0195169 A1 | 8/2008 | Pinter et al. |
| 2008/0200832 A1 | 8/2008 | Stone |
| 2008/0228094 A1 | 9/2008 | Audet et al. |
| 2008/0255464 A1 | 10/2008 | Vincent |
| 2008/0287770 A1 | 11/2008 | Kurzweil et al. |
| 2009/0069703 A1 | 3/2009 | Takla et al. |
| 2009/0222262 A1 | 9/2009 | Kim et al. |
| 2010/0056940 A1 | 3/2010 | Moorman et al. |
| 2010/0063438 A1 | 3/2010 | Bengtsson |
| 2010/0234916 A1 | 9/2010 | Turcott et al. |
| 2011/0046461 A1 | 2/2011 | McKenna |
| 2011/0152957 A1 | 6/2011 | Shaquer |
| 2011/0190648 A1 | 8/2011 | Gu et al. |
| 2011/0306895 A1 | 12/2011 | Nakashima et al. |
| 2012/0165691 A1 | 6/2012 | Ting et al. |
| 2012/0197144 A1 | 8/2012 | Christ et al. |
| 2012/0232417 A1 | 9/2012 | Zhang |
| 2013/0019383 A1 | 1/2013 | Korkala et al. |
| 2013/0069768 A1 | 3/2013 | Madhyastha et al. |
| 2013/0109937 A1 | 5/2013 | Banet et al. |
| 2013/0289424 A1 | 10/2013 | Brockway et al. |
| 2014/0005988 A1 | 2/2014 | Brockway |
| 2014/0135608 A1 | 5/2014 | Gazzoni et al. |
| 2014/0180597 A1 | 6/2014 | Brown |
| 2014/0249431 A1* | 9/2014 | Banet .............. A61B 5/14542 600/485 |
| 2017/0020398 A1* | 1/2017 | Emadzadeh ....... A61B 5/02438 |

FOREIGN PATENT DOCUMENTS

| | | |
|---|---|---|
| WO | 2013/043157 A2 | 3/2013 |
| WO | 2014/123512 A1 | 8/2014 |

OTHER PUBLICATIONS

Boudoulas et al., "The QT greater that QS2 syndrome: a new mortality risk indicator in coronary artery disease," American Journal of Cardiology, 50(6):1229-1235 (Dec. 1982).

Moody et al., "A noise stress test for arrhythmia detectors," Computers in Cardiology, 11:381-384 (1984).

Rao et al, "Discrete Cosine Transform: Algorithms, Advantages, Applications," San Diego, CA: Academic (1990).

J. Woods. Subband Coding, Kluwer Academic Press (1990).

Ball et al., "Dynamical Eigenfunction Decomposition of Turbulent Channel Flow," International Journal for Numerical Methods in Fluids, 12(6):585-604 (Apr. 1991).

Thakor et al., "Applications of adaptive filtering to ECG analysis: noise cancellation," IEEE Transactions on Biomedical Engineering, 38(8):785-794 (Aug. 1991).

Mallat et al., "Singularity Detection and Processing with Wavelets," IEEE Transactions on Information Technology 38:617-643 (1992).

Mallat et al., "Characterization of Signals from Multiscale Edges," IEEE Trans. Pattern Analysis and Machine Intelligence, 14(7):710-732 (Jul. 1992).

Vaidyanathan, "Multirate Systems and Filter Banks," Prentice Hall, Englewood Cliffs, 1993.

Pati et al., "Orthogonal Matching Pursuit: Recursive Function Approximation With Applications to Wavelet Decomposition," in Asilomar Conference on Signals, Systems and Computers, 1:40-44 (Nov. 1993).

Mallat et al., "Matching Pursuits with Time-Frequency Dictionaries," IEEE Transactions on Signal Processing, 41(12):3397-3415 (Dec. 1993).

Comon, "Independent component analysis, a new concept?," Signal Process. Special Issue on Higher Order Statistics, 36(3):287-314 (Apr. 1994).

Donoho et al., "Ideal spatial adaptation by wavelet shrinkage," Biometrika, 81(3):425-455 (1994).

(56) References Cited

OTHER PUBLICATIONS

Xu et al., "Wavelet Transform Domain Filters: A Spatially Selective Noise Filtration Technique," IEEE Transactions on Image Processing, 3(6):747-758 (1994).
Donoho, "Denoising by Soft-Thresholding," IEEE Trans. on Inf. Theory, 41(3):613-627 (May 1995).
Bell et al., "An Information-Maximization Approach to Blind Separation and Blind Deconvolution," Neural Computation, 7:1129-1159. (1995).
Haugland et al., "Cutaneous Whole Nerve Recordings Used for Correction of Footdrop in Hemiplegic Man," IEEE Transactions on Rehabilitation Engineering, 3(4):207-317 (Dec. 1995).
Afonso et al., "Comparing Stress ECG Enhancement Algorithms," IEEE Engineering in Medicine and Biology, pp. 37-44 (May/Jun. 1996).
Cardoso, "Infomax and Maximum Likelihood for Source Separation," IEEE Letters on Signal Processing, 4(4):112-114 (Apr. 1997).
Hilton, "Wavelet and Wavelet Packets Compression of Electrocardiogram," IEEE Transactions on Biomedical Engineering, 44(5):394-402 (May 1997).
Hyvärinen, "New Approximations of Differential Entropy for Independent Component Analysis and Projection Pursuit," In Advances in Neural Information Processing Systems, 10:273-279, MIT Press. (1997).
Sweldens, The lifting scheme: A construction of second generation wavelets. SIAM J. Math. Anal., 29(2):511-546 (Mar. 1998).
American National Standard ANSI/AAMI EC57:1998, Testing and Reporting Performance Results of Cardiac Rhythm and ST Segment Measurement Algorithms.
Tsalaile, et al. "Blind Source Extraction of Heart Sound Signals from Lung Sound Recordings Exploiting Periodicity of the Heart Sound," ICASSP 2008 IEEE, p. 461-464 (2008).
Torres-Pereira, et. al. "A Biotelemetric Implantable Heart-Sound Rate Monitoring System," Proceedings of the XIV International Symposium on Biotelemetry, Apr. 6-11, 1997, Session 6-4, Marburg, German Abstract (1998).
Hyvärinen, "Fast and Robust Fixed-Point Algorithms for Independent Component Analysis," IEEE Transactions on Neural Networks, 10(3):626-634 (May 1999).
Cardoso, "High-Order Contrasts for Independent Component Analysis," Neural Comput., 11(1):157-192 (1999).
Chen et al., "Atomic Decomposition by Basis Pursuit," SIAM J. Scientific Computing, 20(1):33-61 (1999).
Pan et al., "Two Denoising Methods by Wavelet Transform," IEEE Trans. on SP, 47(12):3401-3406 (Dec. 1999).
Michaud et al., "Correlation waveform analysis to discriminate monomorphic ventricular tachycardia from sinus rhythm using stored electrograms from implantable defibrillators," PACE, 22(8):1146-1151 (Aug. 1999).
Mallat, "A Wavelet Tour of Signal Processing," 2nd Ed., 620 pgs., Academic Press, (Sep. 3, 1999).
Langley et al., "Comparison of three measures of QT dispersion," Conference: Computers in Cardiology, pp. 69-72 (Feb. 1999). (Abstract).
Goldberger et al., "PhysioBank, PhysioToolkit, and PhysioNet: Components of a New Research Resource for Complex Physiologic Signals," Circulation 101(23): e215-e220, Jun. 13, 2000).
Lu et al., "Wavelet Compression of ECG Signals by the Set Partitioning in Hierarchical Trees Algorithm," IEEE Transactions on Biomedical Engineering, 47(7):849-856 (Jul. 2000).
Marcellin et al., "An Overview of JPEG-2000," Proc. of IEEE Data Compression Conference, pp. 523-541 (2000).
Saul et al., "Periodic component analysis: An eigenvalue method for representing periodic structure in speech," in NIPS, [Online],, pp. 807-813 (2000). Available: http://www.cs.cmu.edu/Groups/NIPS/00papers-pub-on-web/SaulAllen.pdf.
Taswell, "The What, How, and Why of Wavelet Shrinkage Denoising," Computing in Science and Engineering, vol. 2, No. 3, pp. 12-19 (2000).

Richman et al., "Physiological time-series analysis using approximate entropy and sample entropy", Am. J. Physiol. 278:H2039-H2049 (2000).
Sayood, "Introduction to Data Compression," 2nd ed., Academic Press, Morgan Kaufmann Publishers 2000.
Malik et al., "Measurement, interpretation and clinical potential of QT dispersion," J Am Coll Cardiol, 36(6):1749-1766 (Nov. 15, 2000).
Hyvärinen et al., "Independent Component Analysis: Algorithms and Applications," Neural Networks, 13(4-5):411-430 (2000).
Mayerburg, "Sudden Cardiac Death: Exploring the Limits of Our Knowledge," Journal of Cardiovascular Electrophysiology, 12(3):369-381 (Mar. 2001). (Abstract).
Brennan et al., "Do Existing Measures of Poincaré Plot Geometry Reflect Nonlinear Features of Heart Rate Variability?" IEEE Transactions on Biomedical Engineering, 48(11):1342-1347 (Nov. 2001).
Donoho et al., "Uncertainty Principles and Ideal Atomic Decomposition," IEEE Transactions on Information Theory, 47(7):2845-2862 (Nov. 2001).
Zibulevsky et al., "Blind Source Separation by Sparse Decomposition in a Signal Dictionary," Neural Computation. 13:863-882 (2001).
Oweiss et al, "MASSIT—Multiresolution Analysis of Signal Subspace Invariance Technique: a novel algorithm for blind source separation", Conference on Signals, Systems and Computers, 1:819-823 (2001).
M. Costa, A. L. Goldberger, and C.-K. Peng, Multiscale Entropy Analysis of Complex Physiologic Time Series, Phys. Rev. Lett. 89(6) (Aug. 5, 2002).
Kohler et al., "The principles of software QRS detection," IEEE Engineering in Medicine and Biology Magazine, 21(1):42-57 (2002).
G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).
T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).
D A Clunie, "Extension of an open source DICOM toolkit to support SCP-ECG waveforms," 2nd OpenECG Workshop 2004, Berlin, Germany.
J.-P Martinez, et. al., "A wavelet-based ECG delineator: Evaluation on standard databases," IEEE transactions on biomedical engineering, vol. 51, No. 4, pp. 57 (2004).
Thomsen, M. B., Verduyn, S. C., Stengl, M., Beekman, J. D., de Pater, G., van Opstal, J., et al. (2004). Increased short-term variability of repolarization predicts d-sotalolinduced torsade de pointes in dogs. Circulation, 110, 2453-2459.
Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.
Costa.et. al., "Multiscale entropy analysis of biological signals," Physical Review E 71, 021906:1-18 (2005).
M. Alghoniemy and A. Tewfik, "Reduced Complexity Bounded Error Subset Selection," IEEE Int. Conf. Acoustics, Speech and Signal Processing (ICASSP), pp. 725-728 (Mar. 2005).
S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).
Hamlin RL. Non-drug-related electrocardiographic features in animal models in safety pharmacology. J Pharmacol Toxicol Methods. Jul.-Aug. 2005; 52(1): 60-76.
Van der Linde et al., "A new method to calculate the beat-to-beat instability of QT duration in drug-induced long QT in anesthetized dogs," Journal of Pharmacological and Toxicological Methods 52:168-177 (2005).
R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).

(56) References Cited

OTHER PUBLICATIONS

M. Blanco-Velasco, B. Weng and KE Barner, "A New ECG Enhancement Algorithm for Stress ECG Tests," Computers in Cardiology, vol. 33, pp. 917-920 (2006).
Chen PC, Lee S, Kuo CD. Delineation of T-wave in ECG by wavelet transform using multiscale differential operator. IEEE Trans Biomed Eng. Jul. 2006;53(7):1429-33.
K. Zhang, L.-W. Chan, "An Adaptive Method for Subband Decomposition ICA", Neural Computation, vol. 18, No. 1, pp. 191-223 (2006).
R. Brychta, "Wavelet analysis of autonomic and cardiovascular signals," PhD Dissertation. Vanderbilt University (Aug. 2006).
M. Aminghafari, N. Cheze, J.-M Poggi, "Multivariate de-noising using wavelets and principal component analysis," Computational Statistics & Data Analysis, 50, pp. 2381-2398 (2006).
Aharon, M. Elad and A. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).
Chouakri S.A., et al. ECG signal smoothing based on combining wavelet denoising levels. Asian Journal of Information Technology. vol. 5, pp. 667-677. 2006.
Inan et al. "Robust Neural-Network-Based Classification of Premature Ventricular Contractions Using Wavelet Transform and Timing Interval Features," IEEE Transactions on Biomedical Engineering, 53(12-1):2507-2515 (Dec. 2006). (Abstract).
Smith, "A tutorial on Principal Components Analysis" (Feb. 26, 2002).
Ueno, et al., "Capacitive sensing of electrocardiographic potential through cloth from the dorsal surface of the body in a supine position: a preliminary study," IEEE Transactions on Biomedical Engineering, 54(4):759-766 (Apr. 2007).
K. Oweiss , A. Mason , Y. Suhail , A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).
K. Todros and J. Tabrikian, "Blind Separation of Independent Sources Using Gaussian Mixture Model," IEEE Transactions on Signal Processing, vol. 55, No. 7, pp. 3645-3658 (Jul. 2007).
R. Sameni, M. Shamsollahi, C. Jutten and G. Glifford, "A Nonlinear Bayesian Filtering Framework for ECG Denoising," IEEE Transactions on Biomedical Engineering, vol. 54, No. 12, pp. 2172-2185 (2007).
X. Li, X. Yao, J. Fox, and J. Jefferys, "Interaction Dynamics of Neuronal Oscillations Analysed Using Wavelet Transforms," Journal of Neuroscience Methods 160, pp. 178-185 (2007).
Schimpf et al., "Electromechanical coupling in patients with the short QT syndrome: Further insights into the mechanoelectrical hypothesis of the U wave," Heart Rhythm Society, 5(2): 241-245 (Feb. 2008).
Sarkar et al., "A detector for a chronic implantable atrial tachyarrhythmia monitor," IEEE Trans Biomed Eng., 55(3):1219-1224 (Mar. 2008). (Abstract).
M. Malik, K. Hnatkova, T. Novotny, G Schmidt Subject-specific profiles of QT/RR hysteresis. Am J Physiol Heart Circ Physiol 295:H2356-H2363, 2008.
Akturk et al, "Electron transport and full-band electron phonon interactions in graphene," J. of Applied Physics 103 (2008). (Abstract).
Paredes et al., "Atrial Activity Detection through a Sparse Decomposition Technique," 2:358-362, IBMEI '08 Proceedings of the 2008 International Conference on BioMedical Engineering and Informatics May 27-30, 2008, 2:358-362 (2008). (Abstract).
R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).
O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).
Li et al., "Multiresolution Subband Blind Source Separation: Models and Methods," Journal of Computers, 4(7):681-688 (Jul. 2009).
Afonso et al., Detecting ventricular fibrillation. IEEE Engineering in Medicine and Biology Magazine, vol. 14(2): 152-159 (Mar./Apr. 1995).
Dash et al., "Automatic real time detection of atrial fibrillation," Ann Biomed Eng., 37(9):1701-1709. Epub Jun. 17, 2009. (Sep. 2009). (Abstract).
M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).
R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).
Piccini, et al, "Predictors of sudden cardiac death change with time after myocardial infarction: results from the VALIANT trial," European Heart Journal 2010 31(2):211-221 (Oct. 23, 2009).
J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).
Hadei et al., "A Family of Adaptive Filter Algorithms in Noise Cancellation for Speech Enhancement," International Journal of Computer and Electrical Engineering, 2(2):1793-8163 (Apr. 2010).
Allen et al., "Honeycomb Carbon: A Review of Graphene" Chem. Rev. 110:132-145.(2010).
Attila S. Farkas. et. al. Biomarkers and endogenous determinants of dofetilide-induced torsades de pointes in α1-adrenoceptor-stimulated, anaesthetized rabbits. British Journal of Pharmacology. vol. 161, Issue 7, pp. 1477-1495, Dec. 2010.
Van der Linde et al, "The Electro-Mechanical window: a risk marker for Torsade de Pointes in a canine model of drug induced arrhythmias: ElectroMechanical window and FEAB model," British Journal of Pharmacology 161:1444-1454 (2010).
Daubechies et al., "Synchrosqueezed wavelet transforms: an empirical mode decomposition-like tool," Applied and Computational Harmonic Analysis, 30(2):243-261 (Mar. 2011).
Brockway et al., "Evaluation of an algorithm for highly automated measurements of QT interval," Journal of Pharmacological and Toxicological Methods, 64(1):16-24 (Jul./Aug. 2011). (Abstract).
PhysioBank Archive Index from PhysioNet, the research resource for complex physiologic signals. http://www.physionet.org/physiobank/database/#ecg (downloaded on Aug. 12, 2014).
MIT-BIH Arrhythmia Database from PhysioNet, the research resource for complex physiologic signals. http://www.physionet.org/physiobank/database/mitdb/ (downloaded on Aug. 12, 2014). This database is described in: Moody et al., "The impact of the MIT-BIH Arrhythmia Database" IEEE Eng in Med and Biol, 20(3):45-50 (May-Jun. 2011). (PMID: 11446209).
Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.
Kellermann, et al.,"A mobile phone based alarm system for supervising vital parameters in free moving rats," BMC Research Notes 2012, 5:119, Feb. 23, 2012.
Pan et al., "Accurate Removal of Baseline Wander in ECG Using Empirical Mode Decomposition" Proceedings of NFSI & ICFBI; pp. 177-180 (2007).
http://www.simplehelp.net/2006/09/12/how-to-set-up-outlook-2003-for-email/.
Lee, J., "Time-Varying Coherence Function for Atrial Fibrillation Detection". IEEE Transactions on Miomedical Engineering vol. 60, No. 10, Oct. 2013.
C. Li, C. Zheng, and C. Tai, "Detection of ECG characteristic points using wavelet transforms," IEEE Trans. Biomed. Eng., vol. 42, pp. 21-28, 1995.
V.X. Afonso, W.J. Tompkins, T.Q. Nguyen, and S. Luo, "ECG beat detection using filter banks," IEEE Trans. Biomed. Eng., vol. 46, pp. 192-202, 1999.

(56) References Cited

OTHER PUBLICATIONS

Z. Dokur, T. Olmez, E. Yazgan, and O.K. Ersoy, "Detection of ECG waveforms by neural networks," Med. Eng. Phys., vol. 19, No. 8, pp. 738-741, 1997.
Paul S Addison. Wavelet transforms and the ECG: a review. Physiol. Meas. 26 (2005) R155-R199.
JS. Sahambi', S.N. Tandonz5 R.K.P. Bhatt. Using Wavelet Transforms for ECG Characterization. IEEE Engineering in Medicine and Biology, Jan./Feb. 1997.
Beck et al., "An Inventory for Measuring Depression", Arch Gen Psychiatry, 4:561-571 (Jun. 1961).
Galinier et al., "Depressed low frequency power of heart rate variability as an independent predictor of sudden death in chronic heart failure", Eur. Hrt. J., 21:475-482. (2000).
Ghasemi et al., "A Semi-Automated QT Interval Measurement Based on Wavelet and Energy Analysis," http://physionet.org/challenge/2006/papers.
Pincus, "Approximate entropy as a measure of system complexity", Proc Natl Acad Sci USA, 88:2297-2301 (Mar. 1991).
Quintana et al., "Considerations in the assessment of heart rate variability in biobehavioral research", Frontiers in Physiology, 5(805):1-10 (Jul. 22, 2014).
SadAbadi et al., "A mathematical algorithm for ECG signal denoising using window analysis," Biomed Pap Med Fac Univ Palacky Olomouc Czechoslovakia., 151(1):73-8 (Jul. 2007).
Woo et al., "Patterns of beat-to-beat heart rate variability in advanced heart failure", Am Heart J., 123:704-710 (Apr. 1992).
Igarashi et al., "The Appearance of Human Skin" Technical Report: CUCS-024-05, Dept. of Comp. Sci., Columbia Univ. NY (2005).
Allen et al., "Honey Carbon: A Review of Graphene" 30 Chem. Rev. 110:132-145 (2010).
Cuiwei et al., "Detection of ECG characteristic points using wavelet transforms." Biomedical Engineering, IEEE Transactions on 42(1):21-28 (Jan. 1995). (Abstract).
Figueredo et al., "Compression of Electrocardiogram Using Neural Networks and Wavelets," Computer and Information Science Studies in Computational Intelligence, 131:27-40 (2008).
Billman, "Heart Rate Variability? A Historical Perspective." Frontiers in Physiology (Nov. 29, 2011).
Boerma et al., "Disparity between skin perfusion and sublingual microcirculatory alterations in severe sepsis and septic shock: a prospective observational study." Intensive Care Med., 1294-1298 (2008).
Bramwell et al., The Velocity of the Pulse Wave in Man, Proceedings of the Royal Society of London: Biological Sciences, 93:298-306 (1922).
Buller et al., "Estimation of human core temperature from sequential heart rate observations," Physiological Measurement 34:781-798 (2013).
Cooke et al., "Heart rate variability and its association with mortality in prehospital trauma patients." J Trauma, 363-370 (2006).
Ezri et al., "Pulse Oximetry from the Nasal Septum." Journal of Clinical Anesthesia. 3.6:447-450 (1991).
Griffin et al., Heart rate characteristics and laboratory tests in neonatal sepsis. Pediatrics, A115(4):937-941 (2005).
Joly et al., "Temperature of the great toe as an indication of the seventy of shock." Circulation, 131-8 (1969).
Morey et al., "Feasibility and Accuracy of Nasal Alar Pulse Oximetry." British Journal of Anaesthesia. 112.6:1109-1114 (2014).
Wang et al., "Optimal Depth for Nasopharyngeal Temperature Probe Positioning," Anesthesia and Analgesia. 122.5: 1434-8 (2016).

* cited by examiner

PHYSIOLOGICAL SIGNAL MONITORING AND APPARATUS THEREFOR

OVERVIEW

Monitoring of physiological signals can be important in a variety of applications. However, monitoring can be challenging for various reasons. For instance, access to the individual being monitored can be challenging or burdensome. Real-time monitoring of patients that are remote, such as patients at home or moving in an environment, can be difficult or impossible. Such monitoring can be particularly challenging in military environments and situations, or other situations in which access is difficult. In addition, monitoring in rugged environments, such as those in which movement artifact and vibration, can make obtaining accurate and timely readings difficult. Such environments may be encountered in military situations as noted above, or in civilian situations such as for monitoring trauma patients or patients in rural areas.

Various embodiments are directed to addressing these and other challenges.

The above discussion/overview is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which:

FIG. 3A-3C show respective signals as may be obtained in accordance with one or more embodiments, in which:

FIG. 3A shows correspondence between frequency responses,

FIG. 3B shows relative frequency content, and

FIG. 3C shows division of cycles into windows; and

Figure 1:
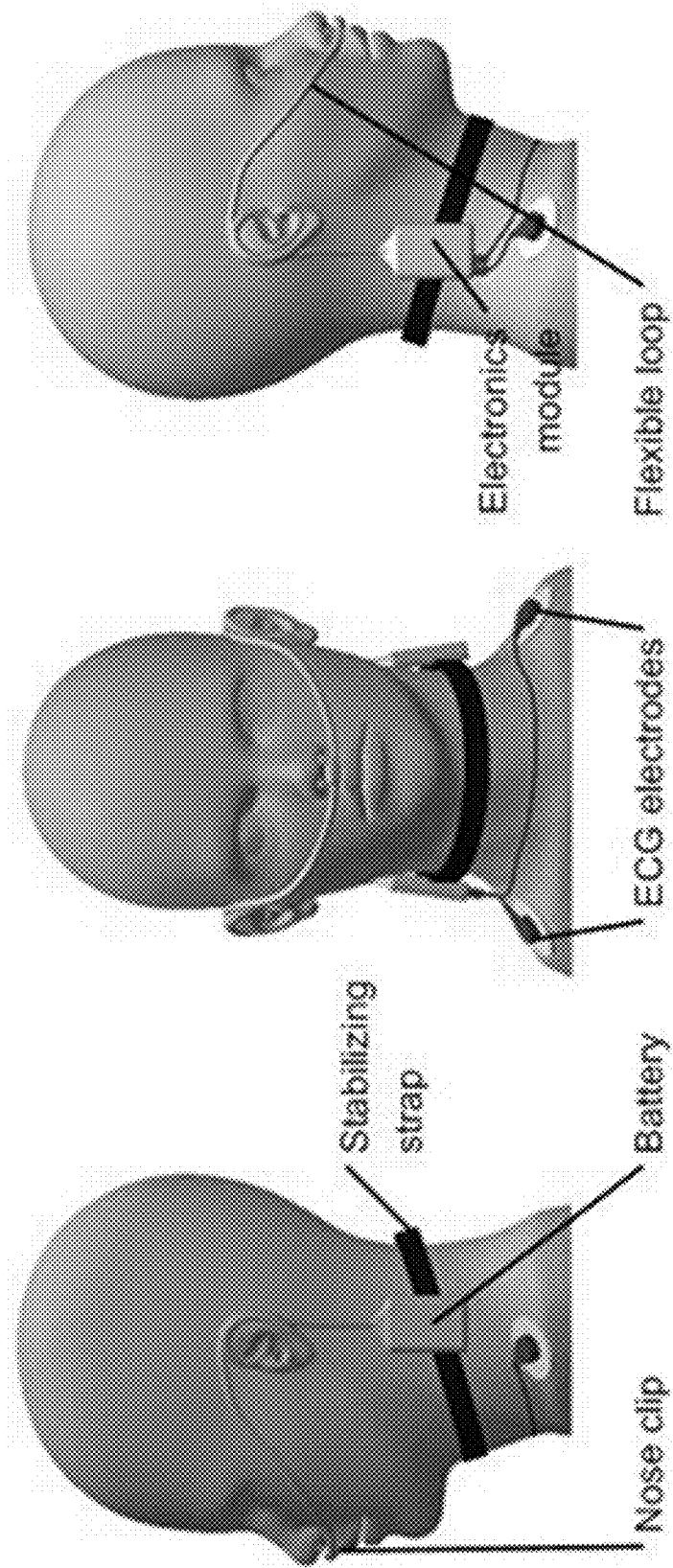
FIG. 1 shows an apparatus and approach as may be implemented for sensing physiological characteristics of a human being, in accordance with one or more embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving sensing physiological signals, and processing such signals. In certain implementations, aspects of the present disclosure have been shown to be beneficial when used in the context of remotely monitoring humans or animals, and related circuitry and/or methods. While not necessarily so limited, various aspects may be appreciated through a discussion of examples using such exemplary contexts.

Various embodiments are directed to wearable devices that provide reliable monitoring of vital signs, such as may be applicable for use with soldiers in the battlefield and during transport to a field hospital. Such monitoring may be continuous. Such devices may monitor pO2, ECG, arrhythmias, heart rate, heart rate variability, respiratory rate, temperature, and movement activity.

In accordance with one or more embodiments, monitoring can be carried out in rugged environments where movement artifact and vibration may otherwise present difficulty in obtaining accurate and timely readings. Such readings may be taken and utilized during transport to triage and delivery of higher levels of medical care. The monitoring can be carried out using a small, easy to use/place, wireless monitor suitable for monitoring mobile patients, such as soldiers in the battlefield and during transport to a care center, civilians in need of trauma care, and patients living with chronic disease in remote locations.

Various embodiments may be implemented for monitoring vital signs, in healthy individuals, in trauma patients, and in chronically ill patients, which can be carried out in remote areas, and in areas in which access is difficult such as in certain confined spaces (e.g., monitoring in potentially dangerous industrial settings). Such embodiments may involve one or more of: a) monitoring patients in step-down clinics, b) diagnosing and monitoring of patients with heart failure to predict decompensation and improve quality of life, c) providing simple, inexpensive, portable and rapid delivery of multiple vital signs to base hospitals from ambulances, which when coupled to computer algorithms may aid in early detection of the more seriously injured trauma victims leading to rapid transport to hospital and/or processing thereat, and d) providing inexpensive vital signs data for humans in remote locations such as for hunters, hikers, soldiers and ranchers.

In accordance with one or more embodiments, an apparatus monitors two or more vital signs from a human being, using a signal acquisition, digitization, and computing module, a wireless communication circuit that transmits such vital signs or related characteristics to a receiver, and circuitry (combined or separate) for sensing two or more vital signs. For instance, the apparatus may a temperature sensor, or electrodes that sense an ECG signal from the human being that may be implemented in accordance with U.S. Pat. No. 8,543,195, which is fully incorporated herein by reference. The apparatus may include monochromatic LEDs and light sensors that sense one or more photoplethysmography (PPG) signals from the human being, and/or electrodes that sense a thoracic impedance signal from the human being. The signal acquisition, digitization, and computing module includes circuitry that performs one or more of removing noise, extracting information useful for diagnosing a health or fitness characteristic of the human being, and compressing information to reduce data volume. Where a temperature sensor is utilized, temperature may be measured via a nasal cannula and/or via insertion into a canal or the outer ear of the human being. In various embodiments, a PPG sensor may be configured attachment to a human being's nasal septum, nasal alar, ear lobe, or for insertion into the human being's canal or ear.

In connection with one or more aspects, it has been recognized/discovered that ascertaining signals in this manner, utilizing an approach to accurately identify desirable signals and/or using two or more vital signs to improve characterization of the human being's physiological condition. Further, low-power wireless communications, such as cellular modems, can be used to transmit such vital signs as processed to provide such an accurate characterization, which requires very low data volume. Such an approach, which may include characterizing the human being's health at the location of the human being, can mitigate the need for complex processing at remote sites, and the associated large data transfer volume. Furthermore, it has been recognized/discovered that, by monitoring and processing two or more vital signs, an improved characterization of the human being's health can be provided, which can also mitigate the need to transmit unnecessary data (e.g., where adverse health conditions can be identified on the spot and without the need to transmit vast amounts of data for analysis). For instance, coupling detection of atrial fibrillation with thoracic impedance monitoring can improve detection of impending heart failure.

The computing module as noted above can be implemented in a variety of manners. In some embodiments, the computing module computes one or more of heart rate, heart rate variability, oxygen saturation, and CO2 saturation. The computing module may detect one or more of the following arrhythmias: atrial fibrillation, tachycardia, pause, and bradycardia (e.g., using approaches as described in U.S. Pat. No. 9,314,181, referenced below). The signal-to-noise ratio (SNR) of an input ECG signal can be increased by >15 dB while maintaining a quality of signal reconstruction (QSR) of >95%, and/or >7x compression can be provided while maintaining QSR of >95% using the computing module. The computing module can be used to detect tachycardia, bradycardia, pause and atrial fibrillation in real time, and/or to extract clinically relevant information from the monitored vital signs and to provide concurrent statistical evaluation of the information to assess and predict the patient's condition in real time.

In certain embodiments, the at least two monochromatic LEDs are utilized to illuminate tissue by transmitting light at a different wavelength relative to another of the at least two LEDs, the light being transmitted by one of the at least two monochromatic LEDs one at a time, in sequence. A sensor is positioned to sense light exiting the tissue, and a signal acquired by the sensor is denoised by digitizing the signal, decomposing respective portions of the digitized signal corresponding to light received on each of the different wavelengths into subcomponents, identifying ones of the subcomponents corresponding to noise, and reconstructing a denoised PPG signal from the subcomponents, based on the identification of the ones of the subcomponents corresponding to noise, using an inverse transform. In this context, identifying the ones of the subcomponents corresponding to noise may include utilizing a blind source separation technique to identify the subcomponents corresponding to noise, or both performing one or more of principal component analysis and independent component analysis on the subcomponents and identifying ones of the subcomponents corresponding to noise based on the one of the principal component analysis and independent component analysis.

Apparatuses characterized herein may be battery powered. In some such implementations, the battery and the signal acquisition, digitization, and computing module are configured and arranged (e.g., size and weight) to be supported at least in part by an anatomical feature of the human being's head or neck, by an adhesive material attached to the human being's chest, or by the human being's arm or chest (e.g., elastically) using a strap. Various embodiments are directed to an apparatus as follows. At least two monochromatic LEDs are configured and arranged to transmit light at a different wavelength relative to the other of the at least two LEDs (e.g., two or three), and to transmit the light one at a time in sequence, for illuminating tissue. A sensor is positioned to sense light exiting the tissue, One or more circuits are implemented to digitize the signal from the sensor, decompose respective portions of the digitized signal corresponding to light received on each of the different wavelengths into subcomponents, identify ones of the subcomponents corresponding to noise, and reconstruct a denoised PPG signal from the subcomponents, based on the identification of the ones of the subcomponents corresponding to noise, using an inverse transform. Such an apparatus may be implemented as a photoplethysmography sensor.

In various embodiments, the subcomponents corresponding to noise are identified utilizing a blind source separation technique. For instance, a set of source signals can be separated from a set of mixed signals without using information or with using little or insignificant information about the source signals or the mixing process. Such an approach may involve performing one or more of principal component analysis and independent component analysis on the subcomponents. Subcomponents corresponding to noise may then be identified based on the one of principal component analysis and independent component analysis.

Certain embodiments address one or more areas for monitoring individuals, such as injured soldiers in the battlefield. One or more embodiments provide componentry that may be implemented to monitor vital signs without removing clothing, such as body armor that may otherwise be removed to expose the chest for placing devices with belt or patch form factors. A particular embodiment involves a nasal cannula or clip can be used to position photoplethysmogram (PPG) and temperature sensors on the nasal septum/nasal sinus, and a flexible tube draped around each ear to support an electronics module and battery, such as shown in FIG. 1. This PPG sensor location facilitates reliable measurements, even when the patient is in shock, and provides stability and resistance to motion artifact. The device may employ stick-on ECG electrodes connected in a manner that will provide broad flexibility of placement. For instance, standard ECG snap electrodes may be connected via DIN40 leads to provide placement flexibility.

Various embodiments are directed to a SpO2 sensor that provides reliable measurements of military or civilian patients, such as those under the care of first responders and during transport. Noise is identified and the identification thereof is used to improve accuracy of measurements during movement or ambient vibration, and under conditions in which unpredictable drops in circulation may occur (e.g. finger and earlobe), such as those characterized in the first reference below. Such embodiments may involve utilization of multi domain signal processing (MDSP) provided by VivaQuant of St. Paul, Minn., as characterized in the patent documents referenced herein, to removing noise and artifact from a photoplethysmography (PPG) signal. A probe may be placed on the nasal septum or alternately, on the wing of the nose, a location known to maintain good circulation during shock. The device transmits a denoised PPG waveform on demand. Since waveform transmission uses significant network bandwidth, the device will also transmit a moving averaged peak-to-peak PPG measurement to provide an indication of tissue perfusion.

Various embodiments minimize network bandwidth for continuous monitoring, facilitating use in civilian care where the need for additional bandwidth drives up cost incrementally and in the battlefield where lack of network bandwidth can compromise timely availability of important information necessary for medical management of injuries. To minimize bandwidth, parameters are extracted from the PPG (e.g. SpO2, peak-to-peak waveform) and ECG signals (e.g. heart rate (HR), and heart rate variability (HRV), and arrhythmias) and highly efficient compression is implemented for on-demand streaming of ECG and PPG waveform.

HRV can be implemented as an indicator for diagnosis and patient status assessment in head trauma cases, and can be implemented using time domain measures or frequency domain approaches [17]. HRV correlates with autonomic system response to a critical condition and can indicate loss of autonomic compensation in trauma [9]. As a soldier's head trauma-induced condition advances, the characteristics of HRV change [9], typically evidenced by increase in high-frequency (HF) energy and reduction in low-frequency (LF) energy. A real-time, computationally efficient wavelet-based analysis is used to provide real-time updates to frequency-based HRV metrics. This approach evaluates individual wavelet scale variability and the relationship between the scales to identify signs that the autonomic system is in distress (as can occur with head trauma). This approach can provide valuable data without necessarily utilizing computationally intense evaluation of long (e.g., 5-minute) segments of RR intervals, minimizing reporting delay and providing an indication of clinically significant abrupt and short-term changes in HRV as the patient's condition evolves.

Certain embodiments facilitate monitoring of multiple vital signs useful for diagnosing and managing trauma victims. Additional sensors and derived parameters can be added, and computing capacity is provided for processing multiple vital signs through machine learning and sensor fusion techniques. Embedded algorithms may locally process acquired information to assist medics in diagnosing the patient's condition and in directing health care resources in a resource-limited environment. Such efforts may leverage the MDSP technology noted above. One or more aspects of which may be implemented in accordance with or otherwise applicable to technology developed with support from NIH grant R44DA041815 "Sensing lead for denoising ambulatory ECG and false positive event reduction." MDSP can be used for removing in-band noise from ambulatory ECGs and to provide very high accuracy of information (e.g. intervals, arrhythmias) extracted from noisy ECGs, and for PPG signals.

Various embodiments are implemented to facilitate monitoring of soldiers exhibiting one or more types of injuries, such as those noted in Table 1 below, along with addressing medical complications associated with those injuries, and the types of vital signs that could be useful in managing those injuries.

TABLE 1

| Medical Complications | Vital Signs for Medical Management |
|---|---|
| Hemorrhage internal | Heart Rate (HR), Systolic BP (SBP), Pulse pressure (PP), Respiratory rate (RR) |
| Non-penetrating head trauma with raised intracranial pressure | Pulse pressure(decrease), Heart Rate variability HF/LF (increased), Temperature (decrease), Systolic BP (decrease) |
| Thoracic injury- pneumothorax Tension-pneumothorax, Hemothorax | $SpO_2$, Thoracic impedance, Tidal volume |
| Sepsis | Central venous pressure (SVP), Blood pressure, Central venous$O_2$/Muscle$O_2$, Temperature (Temp), Non-linear HRV |
| Closed abdominal injury | Heart rate, Heart Rate Variability (HRV), Respiratory rate, Systolic Blood pressure, Pulse pressure |
| Airway obstruction | Thoracic impedance (TI), $SpO_2$, Respiratory rate |
| Burns | $SpO_2$, Respiratory rate, Blood Pressure |
| Crush injuries (building collapse and transport injury) | $SpO_2$, Respiratory rate |

Various embodiments involve one or more apparatuses, which employ one or more aspects as noted below in Table 2.

TABLE 2

| Requirement | Minimum Requirement | Target/Future Requirement |
|---|---|---|
| Vital signs measured | ECG, HR, Arrhythmias, RR, $SpO_2$, Core Temp, HRV, peak-to-peak PPG | ICP, CO2, SBP, bilateral thoracic impedance, PP |
| Volume | < 30 cc excluding radio and antenna[1] | < 20 cc |
| Weight | < 50 gms excluding radio and[1] | |
| Display and alerts | Communicates measurements, derived information, and alerts wirelessly to hand-held device, field hospital, or central monitoring center | Wearable includes beeper and/or LED to announce alerts |
| Frequency of derived observations | HR, Arrhythmias, RR, $SpO_2$, Core (updated every 15 secs) and HRV Temp (updated every 60 secs) | |
| Training required | Experienced combat medic is proficient using the device in < 4 hours training. | |
| Ease of placement | Can be placed in < 120 secs without body armor removal or significant movement of the soldier | |
| Self-test/self-assessment | Device includes mode that automatically evaluates quality of sensor information and notifies medic of issues and suggests corrective actions. | |
| Communication modes | Communicates with battlefield networks with addition of appropriate radio. | |
| Max. data rate req. for continuous PPG & ECG waveform telemetry | < 200 bps network bandwidth (1 ch ECG) | |

TABLE 2-continued

| Requirement | Minimum Requirement | Target/Future Requirement |
|---|---|---|
| Battery life | > 24hours | > 72 hours |
| Battery type | Rechargeable via USB port | Wireless recharge |
| Integrate other sensors (e.g. BP) | | Via secure BlueTooth |

A variety of communication approaches may be implemented for communicating information as noted herein. For instance, small footprint radios such as Bluetooth radios may be utilized, as may be a bulkier secure radio.

Referring again to FIG. 1, an apparatus in accordance with a one or more embodiments may be packaged in a flexible loop that extends from the nasal area and around the ears. The loop is designed so as not to interfere with placement of an ambulatory mask. A clip attached to the nasal septum secures the tube at the nose, and positions light emitting diodes for PPG sensing on the septum, utilizing the well-vascularized nature of the septum and related flow that is relatively immune to loss of blood flow from shock. Two or more (e.g., 800 and 720 nm), and in some embodiments a third (e.g., 680 nm), monochromatic LEDs are positioned on one side of the septum and a (e.g., single) light sensor with filter to reduce ambient light is placed on the opposite side. LEDs are pulsed one at a time sequentially, such as for 500 µsec every 5 msec. LEDs are secured in a small footprint metallic mount to provide uniform temperature and a temperature sensor embedded in the metallic mount is used to compensate for temperature changes that occur during respiration, and may also be used to monitor respiratory rate of the patient.

The clip also supports a nasal cannula for measurement of core temperature. Signals measured and processed can be used to evaluate core temperature from skin temperature or from heart rate as in [3], and address issues when a subject goes into shock, during which skin temperature may no longer provide an accurate indicator of core temperature as noted in [10]. Trauma can be associated with sudden heart rate dips due to vasovagal reaction secondary to hemorrhage, pain, or raised intracranial pressure. Under these conditions the assumption of a linear relationship between heart rate and core temperature may no longer be true, and evaluation thereof can mitigate measurement errors. Some embodiments involve a temperature probe that extends into the nasal cavity for measurement of core temperature, such as by inserting the probe at least 10 cm past the nares to provide temperature measurements equivalent to an esophageal cannula as noted in [4].

The electronics and battery are each housed in modules located on opposite sides of the neck and are electrically interconnected via conductors embedded in the flexible loop. Standard sticky ECG electrodes can be placed on the shoulder, back, or chest. To provide placement flexibility, electrodes may be connected via DIN40 standard snap leads. The electronics and battery housings may be water tight (IP67 rated). An IP67-rated USB connector can be used on the electronic module for firmware image transfers during manufacturing and firmware updates. The platform may be expandable to add additional measurements.

Thoracic impedance measurements can be used as a surrogate for PA pressure, cardiac output, and tissue water. The required instrumentation and signal processing may be implemented, (e.g., to obtain thoracic impedance, two additional electrodes (placed on either side of the chest) may be used and connected to the electronics module by adding two additional DIN40 connectors).

As indicated in Table 1, pulse pressure (PP) can be of value. PP can potentially be estimated from PPG using the Bramwell-Hill [5] relationship.

A capnography ($CO_2$) sensor can be added to the nose clip to measure $CO_2$ in expired air.

If Bluetooth or other short-range communications are considered viable, a BP cuff can be added and connected for communication with the device. BP can be consolidated with other information prior to transmission across the battlefield network.

Figure 2:
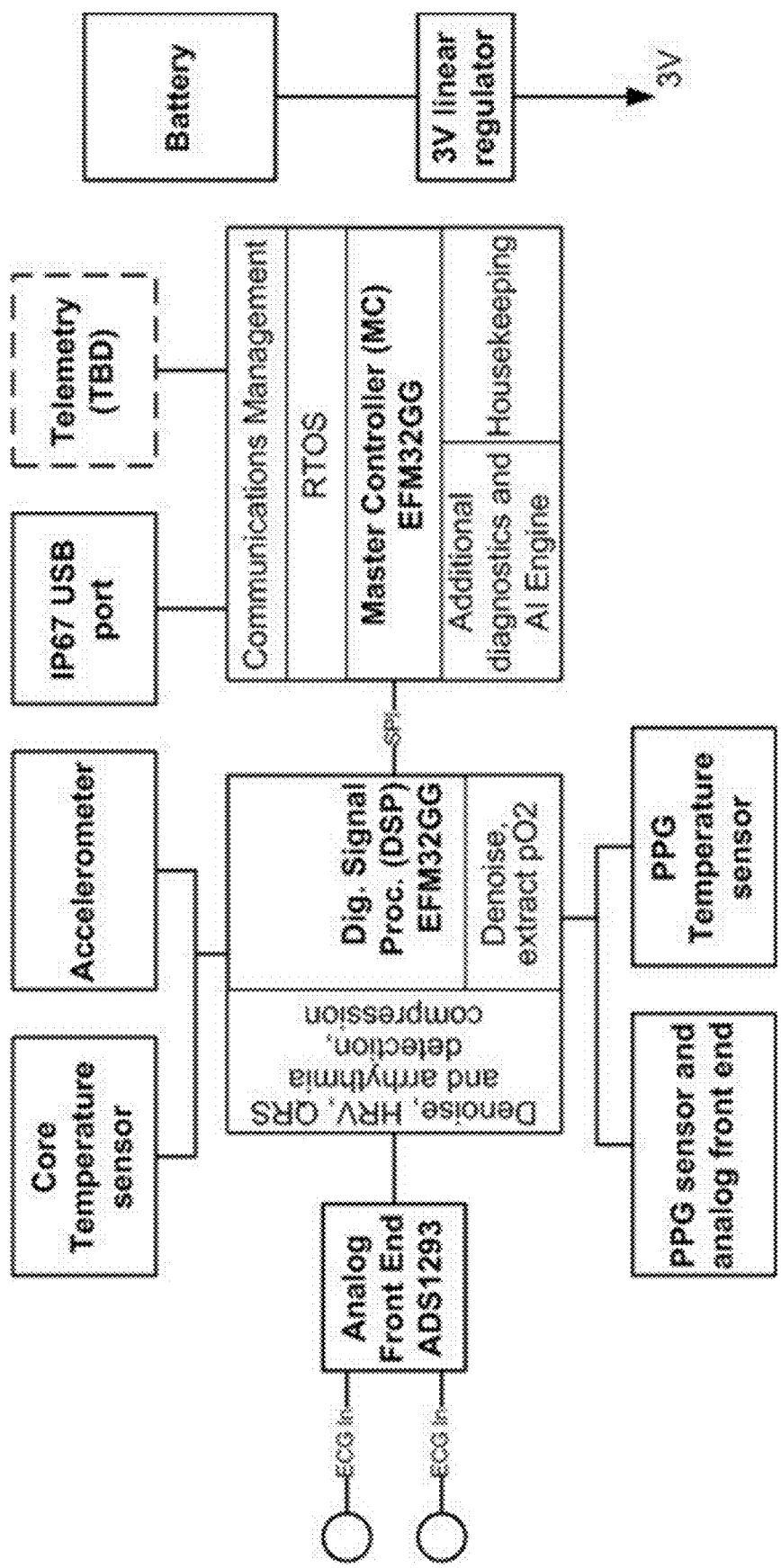
FIG. 2 shows an apparatus as may be implemented in accordance with one or more embodiments.

FIG. 2 shows a block diagram of components for sensing and processing vital sign measurements, in accordance with one or more embodiments. The device employs a dual processor architecture patterned after the VivaQuant RX-1 wearable ECG device. Each EFM32 ARM Cortex M4 processor (Silicon Labs, Austin, Tex.) is configured with 1 MByte RAM). The RX-1 acquires a two channel ECG, removes 95% of noise, identifies arrhythmias, and communicates ECG and arrhythmia information to a central monitoring center via an embedded cellular network link.

The DSP processor shown in FIG. 2 is responsible for acquiring and processing ECG, temperature, activity, and PPG signals. Extracted parameters (e.g. heart rate, respiratory rate, HRV, core temperature, arrhythmias, SpO2, activity, and ECG waveforms) are communicated to the Master Controller (MC) via an SPI interface. The MC is responsible for housekeeping functions, acquisition of temperature and activity, and all communications. In addition, the MC hosts artificial intelligence (AI) algorithms that employ predictive modeling, machine learning, and sensor fusion to evaluate vital sign measurements received from the DSP. The AI implemented on the MC assesses the general health of the patient, suggests how to optimally direct medical care resources, and determines the urgency of care. The AI function may thus improve the effectiveness of combat medics by improving response times and directing their attention where it is needed most to improve the quality of battlefield care.

Motion artifact and noise may be removed from the PPG signal in a variety of manners, to improve the accuracy of SpO2 measurements. Consistent with the above, such embodiments may employ MDSP technology to remove noise and artifact from PPG signals, and improve reliability of SpO2 measurements, and can do so for signals obtained during movement and vibration of the subject and the environment. MDSP provides superb QRS detection accuracy in noisy ECGs and is hence an important enabler of the HRV measurements.

A wavelet-based MDSP algorithm can be thus used to remove in-band noise (e.g., up to 95% of in-band noise) without distorting the ECG. One or more additional wavelet-derived intermediary variables can also be provided via MDSP to improve accuracy. For example, noise tolerance of QRS and ventricular ectopic beat detection benefits from computing the emphasis signal used for detection as a combination of wavelet scales. Intermediary variables are also employed for compression and cardiac interval (e.g. QT interval) measurement. MDSP has been shown to reduce false positive arrhythmia detections by >95% relative to one of the most commonly used mobile cardiac telemetry devices on the market and reduce QT interval measurement variability by 2 to 5×. MDSP is also extremely power efficient, such as when utilizing a wavelet transform. In the embedded ARM Cortex M3 implementation in the RX-1 device, MDSP can be used to denoise and detect arrhythmias in a 2-channel ECG sampled at 200 Hz with less than 200 µA current drain.

In various embodiments, implementation of MDSP for ECG denoising involves decomposition of the ECG recording into subcomponents using a dyadic discrete wavelet transform (DWT) [ref 6].

$$\psi_{m,n}(t) = 2^{-\frac{m}{2}} \psi(2^{-m}t - n) \quad (1)$$

where $\psi$ is a wavelet function, 2 corresponds to the fixed dilation step parameter, integers m and n control the wavelet dilation and translation respectively. The physiologic signal x(t) can then be represented as a combined series expansion of both approximation coefficients S and wavelet (detail) coefficients T.

$$x(t) = \Sigma_n S_{m_o,n} \varphi_{m_o,n}(t) + \Sigma_m \Sigma_n T_{m,n} \psi_{m,n}(t) \quad (2)$$

The wavelet transform represents a signal in the time-scale domain and is well suited to analyzing signals with quasi-periodic waves with time varying frequency content typical in a PPG or ECG signals. MDSP denoising is utilized to leverage the physiologic sparsity of PPG and ECG signal frequency content.

Figure 3A:
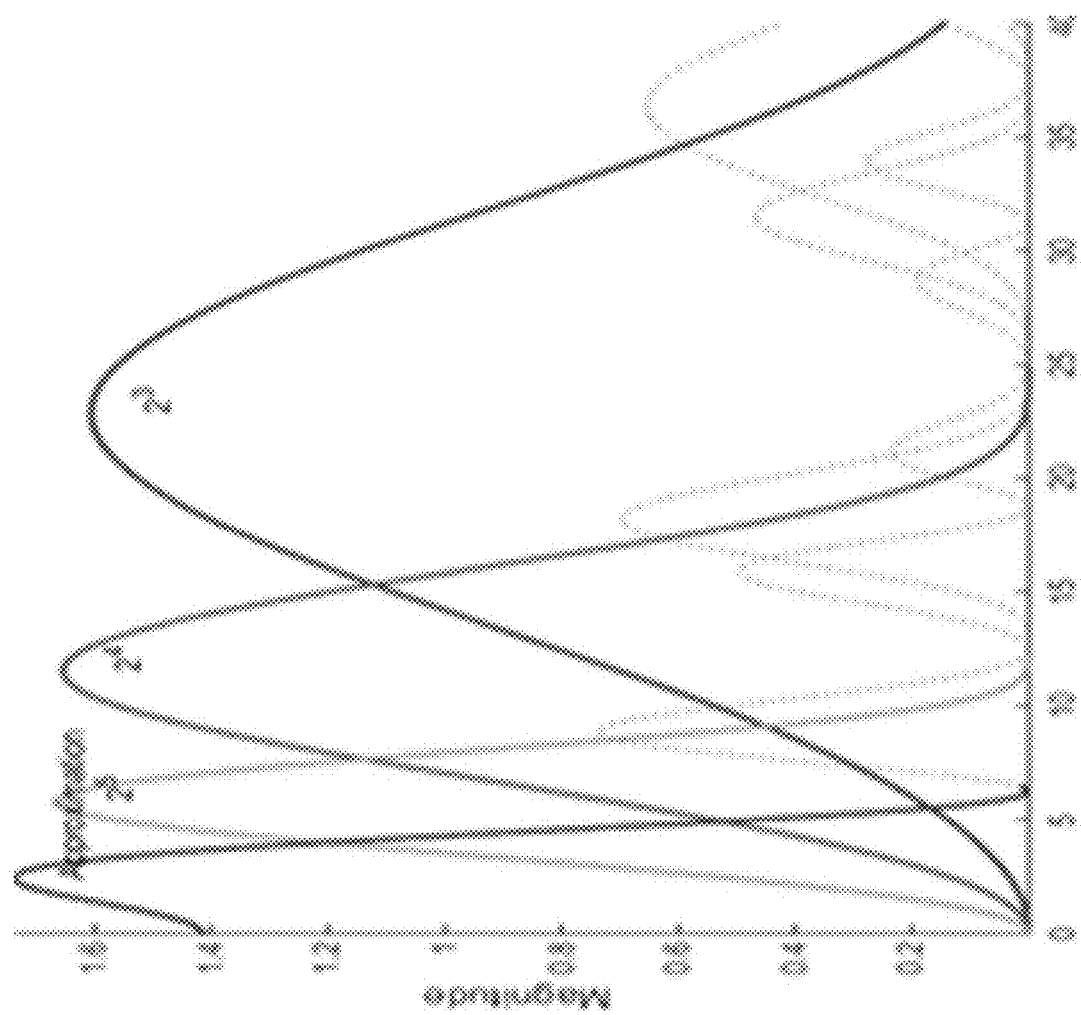

FIG. 3A shows correspondence between frequency responses of DWT filters for sampling rate 200 Hz and relative power spectra of ECG components, with main lobes shown in solid line and side lobes in dotted line. The cardiac cycle is divided into 2 windows; one around the QRS (wide bandwidth window) and the other around the remainder of the cardiac cycle (low-bandwidth window) [7].

Figure 3B:
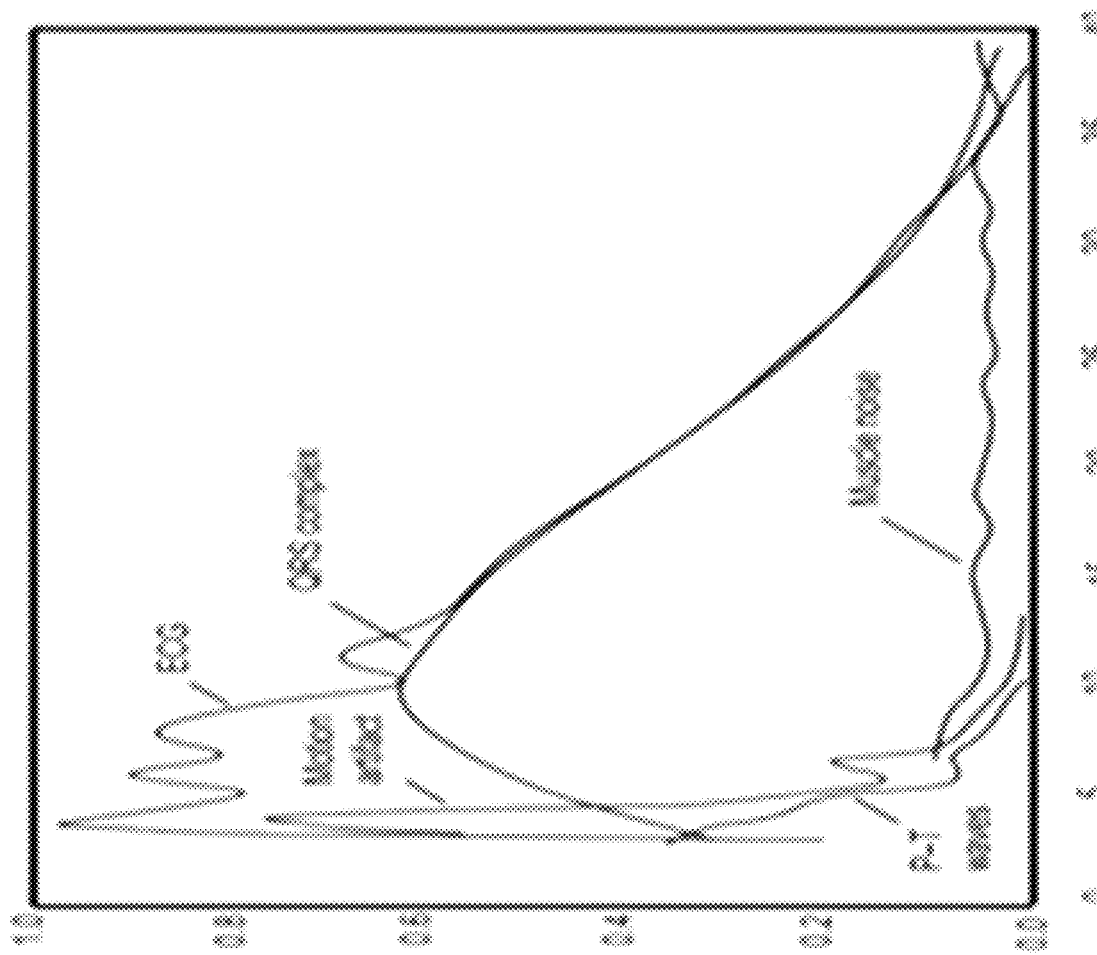
Figure 3C:
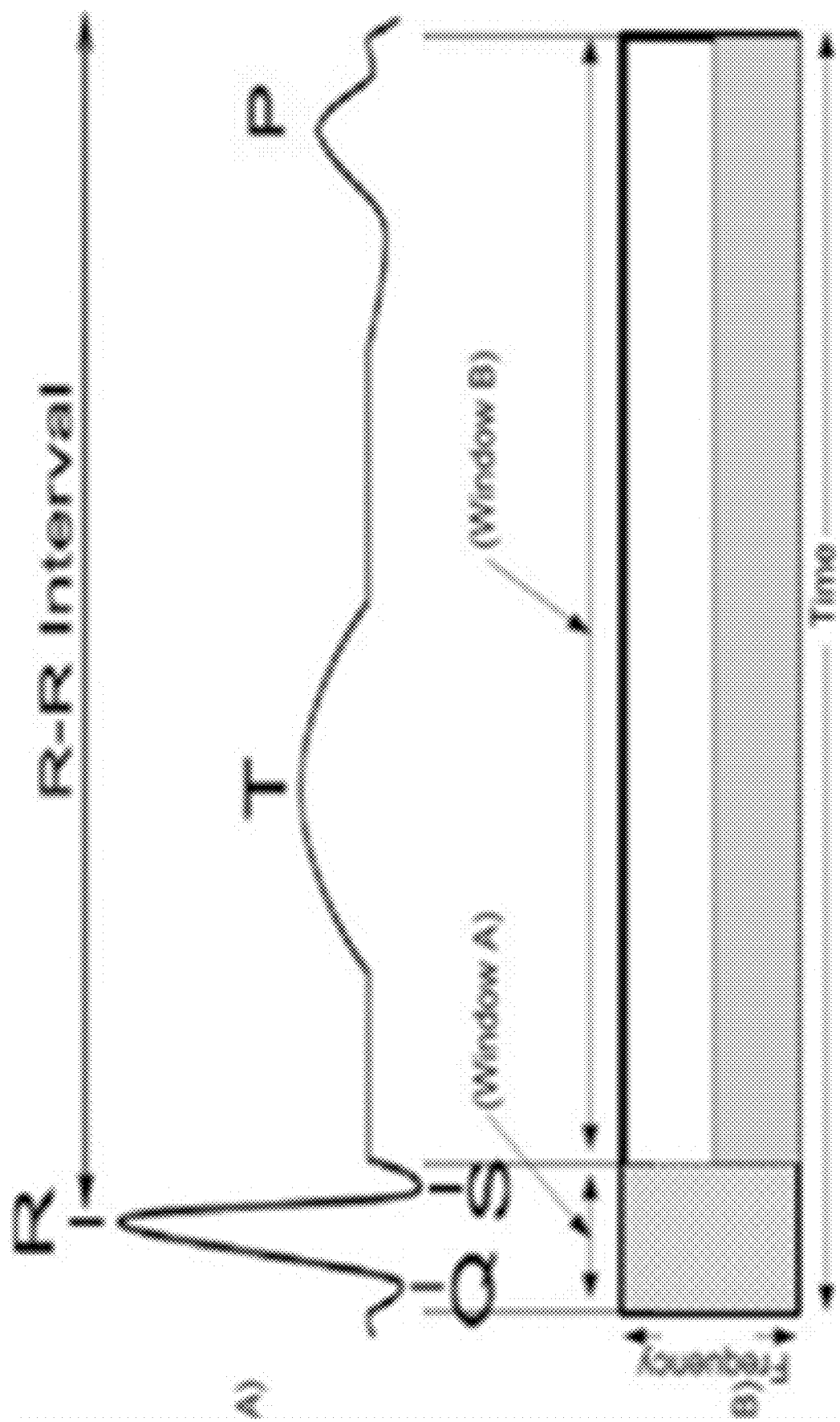

FIG. 3B illustrates relative frequency content of different components of the ECG waveform, as may be implemented in accordance with one or more embodiments. While the QRS portion of the ECG is wide-band, the rest of the signal energy is concentrated in the low-frequency domain. Once QRS locations are identified, each cardiac cycle is divided into two windows, as shown in FIG. 3C; Window A (wide bandwidth window) around the QRS and Window B (low-bandwidth window) around the remainder of the cardiac cycle. Non-stationary filtering is used to remove subcomponents corresponding to higher-frequencies from Window B. The residual subcomponents are reconstructed using an inverse transform to create an ECG signal free of most in-band noise and without distortion.

Various embodiments involve denoising approaches that mitigate false positive detection of T-waves and false negative detection of ventricular ectopic beats, utilizing a two-step MDSP process [6]. The first step favors sensitivity at the expense of positive predictivity (PPV) and involves computing an emphasis signal as a linear or non-linear combination of the matching scales. The combination of the matching wavelet scales can be dynamically adjusted to avoid many of the pitfalls of emphasis signals and respond to changing conditions. MDSP also employs adaptive QRS detection thresholding by continuously measuring the noise level and using it as a floor for detection threshold. The second step for QRS detection uses the denoised signal with parameters adjusted to favor PPV in order to remove false positive detections. PPG processing may employ many of the same noise removal techniques used for ECG, and a combination of MDSP noise removal, noise detection and blanking, and sensor fusion. Redundancy in the collected signals may be used to reduce their sensitivity to noise. Specifically, PPG waveforms can be collected using three wavelengths, selected to improve contrast between oxygenated and deoxygenated hemoglobin. Computation of SpO2 involves separating PPG waveforms into AC and DC components which can be efficiently accomplished with a wavelet transform. At the wavelet scales with the central frequency corresponding to the heart rate band, principal component analysis (PCA) is performed to orthogonalize noise and signal. PCA performance may be improved with additional waveforms, by increasing dimensionality to suppress distortions. The component with the largest energy in the time windows synchronized with the QRS complex locations is selected as the AC signal component. The inverse wavelet transform is performed on the wavelet detail coefficients to reconstruct the AC signal. The AC amplitude is estimated by calculating median of cardiac cycles, timed according to the detected QRS complexes. An intermediate step of the MDSP algorithm may be implemented to remove baseline wander that emulates a filter bank. This step can be further enhanced by applying a noise cancelling filter that utilizes data from the accelerometer as a reference. The MDSP algorithm can also be used to assess noise level on a real-time basis [7]. When the noise level is detected to be too high for a reliable SpO2 measurement, the signals are blanked out for calculation to avoid reporting inaccurate measurements.

Figure 4:
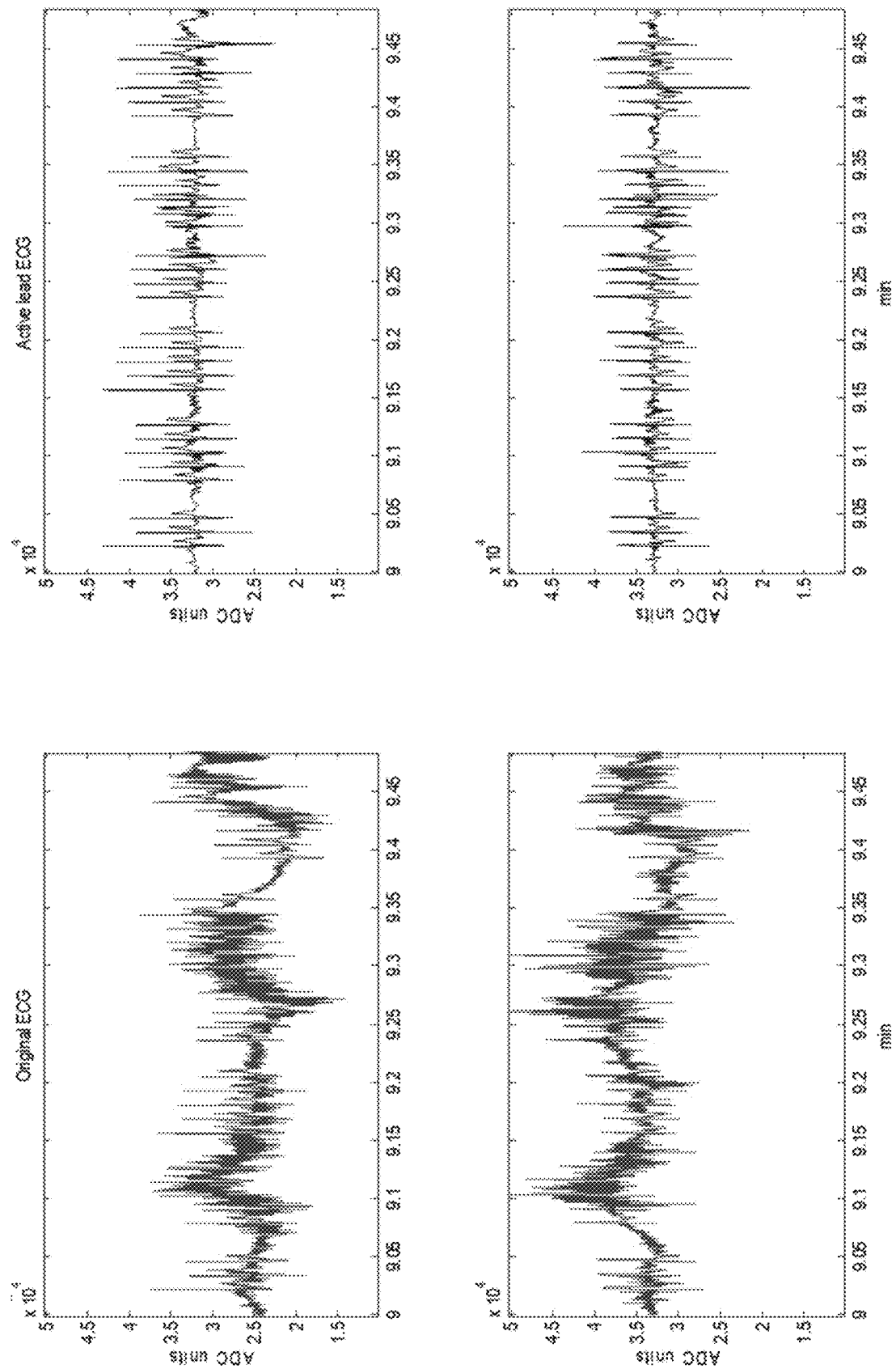
FIG. 4 shows plots of signals as ascertained and denoised in accordance with one or more embodiments.

FIG. 4 shows MDSP denoising in an ECG strip with noise added per EC-57 standard, before (left) and after (right) MDSP filtering, as may be implemented in accordance with one or more embodiments. For instance, a similar approach may be implemented for PPG denoising, using pseudoperiodic characteristics of a PPG signal.

One or more embodiments involve an HRV Algorithm for use in diagnosis and monitoring in head trauma. A measurement of heart rate variability (HRV) is provided and used to facilitate assessing autonomic compensation following head trauma. HRV correlates with autonomic system response to critical conditions and can warn of loss of autonomic compensation in severe distress [9]. For instance, as a soldier goes through the stages of initial shock and trauma to cardiac compromise, the characteristics of HRV change [9], evidenced by increase in high-frequency (HF) energy and reduction in low-frequency (LF) energy. Non-linear methods are used to assess interactions of neural regulatory mechanisms involved in the cardiovascular system. These methods, developed in nonlinear systems theory, can be used to reveal subtle abnormalities in cardiac autonomic regulation that may not be uncovered by other measures of heart rate variability. Multiscale analysis is employed, which utilizes non-linear metrics developed for analysis of complex non-linear systems, such as detrended fluctuation analysis (DFA) and multiscale entropy (MSE), to quantify changes in HR trends characteristic of loss of autonomic compensation in severe distress. Multi-scale analysis can also be used to differentiate factors that can contaminate traditional frequency based metrics when signal character changes. For example, such approaches can be used to identify patients in sepsis with compromised survival that experience reduced low frequency energy of HRV, yet the heart rate trend shows distinctive dips at the advanced stages [18]. These dips in HR artificially increase the low frequency energy, thus contaminating the LF calculation. These distinctive features can be differentiated with multi-scale analysis of wavelet dynamics using techniques such as DFA and MSE.

Such non-linear metrics can be coupled with the computationally efficient wavelet decomposition noted herein to enable real-time implementation in embedded systems. Such approaches may be implemented in a manner consistent with those utilized for extracting patterns in the multi-scale dynamics of HR trend for atrial fibrillation detection [5], with extraordinary performance (100/96% Se/PPV) for events 60 seconds and longer in the MIT-BIH arrhythmia database.

A variety of components can be implemented to provide aspects of one or more embodiments herein, and may involve one or more of the following. A flex circuit acquires PPG and accelerometer data from the nasal septum and from the wing of the nose. The circuit is attached to a clip and used in a later task to acquire data from human subjects to generate a variety of PPG recordings obtained under various conditions (e.g. vibration noise, movement noise, stable) to investigate signal processing algorithms. The circuit includes two or three monochromatic light sources (e.g. 680, 720, and 800 nm) and a light sensor and filter to remove ambient light. The circuit is constructed such that the light sources and the light sensor can be placed on opposite sides of either the nasal septum or the wing of the nose. ECG may captured separately using an off-the-shelf front end with USB interface. PPG, ECG, and accelerometer data are captured synchronously using a data acquisition system, such as those driven by Matlab software. The data acquisition system is used to acquire human data with modifications to accommodate specific needs.

A variety of algorithms can be implemented, in accordance with one or more embodiments. An algorithm processes PPG, ECG, and accelerometer data acquired and derives estimates of SpO2. In addition to signals from two or three different colored light sources, the algorithm uses ECG and accelerometer data. The algorithm decomposes the PPG signals and apply principal component analysis (PCA) to the wavelet scales to orthogonalize noise and signal. Components of the wavelet scales corresponding to useful signal are used to reconstruct the denoised PPG signal. A filter bank is applied to remove baseline wander. The output of the accelerometer is used as a reference signal for noise cancellation. The QRS detections from the ECG signal are used as an aid in accurately identifying PPG cardiac cycles for measuring pulse amplitude. Individual PPG pulse waves are signal averaged to increase SNR and used for estimating the level of tissue perfusion and for computing SpO2. SpO2 is computed using the signal averaged PPG AC and DC components at different wave lengths. Wavelet analysis may be implemented using technology noted in the references cited herein, as noted in connection with the MDSP and other VivaQuant technologies, to assure that it can be implemented efficiently in embedded code. For MDSP ECG processing, wavelet transform operations for decomposition and reconstruction may account for about 70% of computational operations. Computational operations for PPG denoising may be similarly distributed and hence the computational load for PPG may similar to that for ECG.

Evaluation of algorithms developed in accordance with one or more embodiments may be involve wavelet decomposition and reconstruction using technologies referenced herein, such as those available from VivaQuant, and implemented in one or more experimental type embodiments as follows. The RR trend is interpolated and upsampled to generate an equispaced time series. The RR series is decomposed using a wavelet transform. An approximation of frequency domain metrics using wavelet scales is computed and compared to traditional frequency domain HRV metrics. Non-linear metrics such as DFA and MSE are computed using wavelet scales. HRV results are compared to the HRV results from the public domain HRV algorithm available from Physionet computed on the MIT-BIH arrhythmia ECG database. This provides a comparison for patients not subjected to head trauma. In some implementations, a source of ECG recordings from head trauma patients suitable for algorithm validation are utilized, as clinical observations may be as well. For instance, ECG data from six such patients can be processed with recordings to assess algorithm performance, or data from swine before and after head trauma may be evaluated. HRV is computed on (e.g., six of) these recordings to assess changes following induction of trauma and the results evaluated as a qualitative assessment of algorithm performance.

In certain experimental embodiments, data is collected from human subjects for a PPG algorithm as noted herein. Enrolled subjects can be evenly distributed between three groups: dark skin, light skin, and skin with moderate melanin content. Measurements of thickness of the nasal septum and nasal wing can be obtained from each subject. ECG electrodes can be attached to each subject in a modified Lead II orientation (i.e. one electrode at the upper right chest at the clavicle and one electrode at approximately V5). A commercialized SpO2 sensor can be attached to an ear lobe. The instrument readout can be positioned in the field of view of the video camera so SPO2 measurements are recorded for the duration of data collection of each subject. A PPG sensor can be positioned on the nasal septum with the subject supine. Data collection can be initiated for a minimum of 5 minutes. The subject can be asked to perform a number of movements of the body and head simulating movement during transportation, and each subject can be asked to hold their breath for as long as can be tolerated to induce a drop in SpO2. The recording is then terminated. The PPG sensor will then be positioned on the wing of the nose and the data collection will again be initiated for at least 5 minutes with all maneuvers repeated.

In another embodiment, a wearable device is worn by a patient for continuously monitoring and diagnosing various pathologies from an electrocardiogram. A characteristic of these devices is diagnostic yield, the ability of a device to sense and report a clinically relevant finding to a clinician so it can be used to design a treatment regimen for the patient. Clinically relevant findings are possible if the patient is wearing the device when the arrhythmia event occurs. Therefore, patient compliance is useful for achieving high diagnostic yield. In order to encourage patient compliance, the device is desirable small, comfortable, and easy to wear and use.

To expand the clinical utility of these devices (e.g., implemented in accordance with one or more embodiments), multiple sensors may be included. Sensors are often communicatively coupled to an electronic circuit module that amplifies and digitizes the signal from the sensors and includes one or more computing elements for digitally processing the signal to remove noise and extract clinically useful information, similar to that described in U.S. Pat. Nos. 8,543,195, 8,688,202, and/or 9,314,181, all of which are fully incorporated herein by reference. In one embodiment, such a computing element is used to evaluate the outputs from multiple sensors to improve the accuracy and breadth of diagnostic information provided. In another embodiment, the computing element includes the capability of compressing the data to reduce the data volume and power consumption of the device. Reduced power consumption can enable increased battery life, a reduction in physical size of the device, or both. In yet another embodiment, the device also includes a wireless communications module to communicate information derived from the sensors to a receiver located remotely from the device.

Assessment of arrhythmias can be accomplished using ECG. ECG can also be used to measure a respiratory signal and detect sleep apnea. Such approaches may involve, for example, aspects characterized in FIG. 15 and the accompanying text in U.S. Pat. No. 8,632,465, which is fully incorporated herein by reference. Accurate heart failure (HF) decompensation prediction in a broad population of patients may require that addition vital signs be measured. In one embodiment, thoracic impedance is used to assess fluid on the lungs that accumulates before and during HF decompensation as a means to predict HF decompensation. In another embodiment, $pO_2$ and $pCO_2$, indicators of tissue perfusion, are used to predict HF decompensation. $pO_2$ and $pCO_2$ are impacted by heart function and often decline in advance of HF decompensation. In yet another embodiment, atrial fibrillation burden or occurrence is employed as a means of predicting HF decompensation. In yet another embodiment heart sounds, electromechanical windows, and respiratory characteristics are used to predict heart failure decompensation.

Accuracy of HF decompensation prediction can often be improved by evaluating the signal provided by multiple sensors. In one embodiment, two or more of atrial fibrillation burden, $pO_2$, a characteristic of respiration such as respiratory rate, heart sounds, electromechanical window, and thoracic impedance are measured and concurrently assessed and statistically evaluated to improve prediction of HF decompensation.

Predicting HF decompensation is important because HF decompensation can lead to expensive hospitalization and poor patient quality of life. By predicting the occurrence, actions can be taken to treat the condition and reverse the progression of HF decompensation, thereby preventing hospitalization. The use of combinations of vital sign measurements can improve prediction accuracy. Such an embodiment or embodiments may be implemented in accordance with aspects of U.S. Pat. No. 8,688,202, which is fully incorporated herein by reference. For instance, aspects in the '202 patent related to incorporating an acoustical sensor into an ECG electrode may be utilized to facilitate prediction accuracy in the above context.

Wearable devices are available in various formats, as may be implemented in accordance with one or more embodiments: a) patch style where the recording device is attached to the skin with an adhesive patch with integrated ECG electrodes and sensors, b) a chest strap style where the recording device is attached or embedded in a strap worn around the chest with integrated ECG electrodes and sensors, c) a pendant style where the recording device is suspended from the neck using a lanyard. Lead wires connect the recording device to ECG electrodes adhered to the skin as well as other sensors, and d) button style where the recording device is attached to ECG electrodes adhered to the skin, often with a lead wire connecting the recording device to one or more electrodes located remote form the button.

Patients often have personal preferences for one type of device vs. another. A certain type of device may be more comfortable for a given patient than another based upon size, BMI, breast size, and other factors. In one embodiment, the electronic circuit module is designed to be used in more than one format. For example, the same electronic circuit module can be attached to a patch-style device or a device worn on a chest strap. The patient can decide, in collaboration with his/her physician, which approach will be more comfortable. The electronic circuit module that then be attached to the appropriate supporting element (e.g. patch or strap) for the patient to wear.

In one embodiment, a device in accordance with one or more embodiments herein includes signal processing features capable of data reduction and ultra-low power operation. These signal processing features include:
  Ability to reduce in-band noise by up to 25 dB (denoising) while preserving morphology (QSR>95%)
  Loss-less compression >7×
  Ability to implement real-time acquisition at a 200 Hz sampling rate, denoising, detection of bradycardia, tachycardia, pause, and atrial fibrillation for <1 mA average current consumption.
  Wirelessly communicate arrhythmia findings over a cellular network for a typical mobile cardiac telemetry use case for <2 mA average current consumption.

In one embodiment, the electronic circuit module and battery for a device including the above features is <27 cc in volume and has a battery life of >10 days when using a fully charged standard lithium ion rechargeable cell.

Features characterized above may be implemented in accordance with one or more of the various patent documents incorporated by reference herein. For instance, various embodiments may be implemented in accordance with aspects characterized in U.S. Pat. No. 9,706,956, and/or with any of the underlying patent documents noted therein and to which priority is claimed, and all of which are fully incorporated herein by reference. For instance, various approaches to denoising, such as by decomposing signals into subcomponents, evaluating those subcomponents and reconstructing a denoised signal from selected ones of those subcomponents based on the analysis, can be implemented to facilitate aspects of the instant disclosure. One or more embodiments, may be implemented in connection with approaches characterized in one or more of the following references, all of which hare fully incorporated by reference herein:
1. Pulse Oximeter Training Manual. World Health Organization, Geneva, Switzerland 2011.
2. Buller M J, Tharion W J, Cheuvront S N, Montain S J, Kenefick R W, Castellani J, Latzka W A, Roberts W S, Richter M, Jenkins O C, Hoyt R W. (2013) *Estimation of human core temperature from sequential heart rate observations*. Physiological Measurement 34 781-798.
3. Wang M, et al. "Optimal Depth for Nasopharyngeal Temperature Probe Positioning." *Anesthesia and Analgesia*. 122.5 (2016): 1434-8
4. Bramwell, J. Crighton and Hill, A. V., The Velocity of the Pulse Wave in Man, Proceedings of the Royal Society of London: Biological Sciences, 93:298-306, 1922.
5. U.S. Pat. No. 9,314,181 Brockway, M and Brockway B. Method and Apparatus for Detection of Heart Beat Characteristics. 2016
6. U.S. Pat. No. 9,408,549 Brockway, M Detecting Fiducial Points in Physiological Signals. 2016
7. U.S. Pat. No. 8,632,465 Brockway, M PHYSIOLOGICAL SIGNAL DENOISING ("MDSP") 20
8. Boerma E C, Kuiper M A, Kingma W P, Egbers P H, Gerritsen R T, Ince C. "Disparity between skin perfusion and sublingual microcirculatory alterations in severe sepsis and septic shock: a prospective observational study." Intensive Care Med., 2008: 1294-8.
9. Cooke W H, Salinas J, Convertino V A, Ludwig D A, Hinds D, Duke J H, Moore F A, Holcomb J B. "Heart rate variability and its association with mortality in prehospital trauma patients." J Trauma, 2006: 363-70.

10. Joly H R, Weil M H. "Temperature of the great toe as an indication of the severity of shock." Circulation, 1969: 131-8.
11. Ezri T, et al. "Pulse Oximetry from the Nasal Septum." Journal of Clinical Anesthesia. 3.6 (1991): 447-50.
12. Morey T E, et al. "Feasibility and Accuracy of Nasal Alar Pulse Oximetry." British Journal of Anaesthesia. 112.6 (2014): 1109-14.
13. M. L. Hilton. Wavelet and wavelet packets compression of electrocardiogram. IEEE Transactions on Biomedical Engineering, 44(5):394-402, May 1997.
14. Z. Lu, D. Y. Kim, and W. A. Pearlman. Wavelet compression of ECG signals by the set partitioning in hierarchical trees algorithm. IEEE Tran-sactions on Biomedical Engineering, 47(7):849-856, July 2000.
15. S. C. Tai, C. C. Sun, and W. C. Tan, "2-D ECG compression method based on wavelet transform and modified SPIHT," IEEE Trans. Biomed. Eng., vol. 52, no. 6, pp. 999-1008, June 2005
16. Marcellin M., et al., An Overview of JPEG-2000, Proc. of IEEE Data Compression Conference, pp. 523-541, 2000
17. Billman, G. E. (2011). Heart Rate Variability? A Historical Perspective. Frontiers in Physiology, 2.
18. Griffin M P, Lake D E, Moorman J R. Heart rate characteristics and laboratory tests in neonatal sepsis. Pediatrics. 2005; 115(4):937-41.

Various blocks, modules or other circuits may be implemented to carry out one or more of the operations and activities described herein and/or shown in the figures. In these contexts, a "block" (also sometimes "logic circuitry" or "module") is a circuit that carries out one or more of these or related operations/activities (e.g., obtaining a signal, denoising a signal, or generating an output indicative of a physiological characteristic). For example, in certain of the above-discussed embodiments, one or more modules are discrete logic circuits or programmable logic circuits configured and arranged for implementing these operations/activities, as in the circuit modules shown in FIG. 2. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform these operations/activities.

Based upon the above discussion and illustrations, those skilled in the art will readily recognize that various modifications and changes may be made to the various embodiments without strictly following the exemplary embodiments and applications illustrated and described herein. For example, applications related to military situations can be implemented in other scenarios, such as for remote monitoring of the health of a human or animal. In addition, the various embodiments described herein may be combined in certain embodiments, and various aspects of individual embodiments may be implemented as separate embodiments. Such modifications do not depart from the true spirit and scope of various aspects of the invention, including aspects set forth in the claims.

What is claimed is:

1. An apparatus configured and arranged to monitor two or more vital signs from a human being, the apparatus comprising:
    two or more sensing circuit components, including at least two of the following:
        at least two electrodes configured and arranged to sense an ECG signal from the human being,
        at least two monochromatic LEDs and light sensors configured and arranged to sense one or more photoplethysmography (PPG) signals from the human being,
        a temperature sensor, and
        at least two electrodes configured and arranged to sense a thoracic impedance signal from the human being;
    a signal acquisition, digitization, and computing module, including circuitry, configured and arranged to compress information to reduce data volume to provide >7× compression while maintaining QSR of >95%, via the two or more sensing circuit components, to produce data characterizing the two or more vital signs; and
    a wireless communications circuit configured and arranged to transmit the data characterizing the two or more vital signs to a receiver.

2. The apparatus of claim 1, wherein the computing module is configured and arranged to compute one or more of heart rate, heart rate variability, oxygen saturation, and $CO_2$ saturation.

3. The apparatus of claim 2, wherein the computing module is configured and arranged to detect one or more of the following arrhythmias: atrial fibrillation, tachycardia, pause, and bradycardia.

4. The apparatus of claim 1, wherein the computing module is configured and arranged to perform one or more of removing noise and extracting information useful for diagnosing a health or fitness characteristic of the human being.

5. The apparatus of claim 1, wherein the computing module is configured and arranged to detect tachycardia, bradycardia, pause and atrial fibrillation in real time.

6. The apparatus of claim 1, wherein the computing module is configured and arranged to extract clinically relevant information from the monitored vital signs and to provide concurrent statistical evaluation of the information to assess and predict the patient's condition in real time.

7. The apparatus of claim 1, wherein each of the at least two monochromatic LEDs is configured and arranged to illuminate tissue by transmitting light at a different wavelength relative to another of the at least two LEDs, the light being transmitted by one of the at least two monochromatic LEDs one at a time, in sequence, further including:
    a sensor positioned to sense light exiting the tissue; and
    circuitry configured and arranged to denoise a signal acquired by the sensor, by digitizing the signal;
        decomposing respective portions of the digitized signal corresponding to light received on each of the different wavelengths into subcomponents;
        identifying ones of the subcomponents corresponding to noise; and
        reconstructing a denoised PPG signal from the subcomponents, based on the identification of the ones of the subcomponents corresponding to noise, using an inverse transform.

8. The apparatus of claim 7, wherein identifying the ones of the subcomponents corresponding to noise includes utilizing a blind source separation technique to identify the subcomponents corresponding to noise.

9. The apparatus of claim 7, wherein identifying the ones of the subcomponents corresponding to noise includes:
performing one or more of principal component analysis and independent component analysis on the subcomponents, and
identifying ones of the subcomponents corresponding to noise based on the one of the principal component analysis and independent component analysis.

10. The apparatus of claim 1, wherein the temperature sensor is configured and arranged to measure temperature via a nasal cannula.

11. The apparatus of claim 1, wherein the temperature sensor is configured and arranged to be inserted into a canal or the outer ear of the human being.

12. The apparatus of claim 1, further including a PPG sensor configured and arranged for attachment to the human being's nasal septum, nasal alar, ear lobe, or for insertion into the human being's canal or ear.

13. The apparatus of claim 1, wherein
the apparatus includes a battery, and
the battery and the signal acquisition, digitization, and computing module are configured and arranged to be supported at least in part by an anatomical feature of the human being's head.

14. The apparatus of claim 1 wherein
the apparatus includes a battery, and
the battery and the signal acquisition, digitization, and computing module are configured and arranged to be supported at least in part by an anatomical feature of the human being's neck.

15. The apparatus of claim 1 wherein
the apparatus includes a battery, and
the battery and the signal acquisition, digitization, and computing module are configured and arranged to be supported by an adhesive material attached to the human being's chest.

16. The apparatus of claim 1 wherein
the apparatus includes a battery and a strap, and
the battery and the signal acquisition, digitization, and computing module are configured and arranged to be supported by the human being's arm via the strap.

17. The apparatus of claim 1 wherein
the apparatus includes a battery and a strap, and
the battery and the signal acquisition, digitization, and computing module are configured and arranged to be supported by the strap with the strap at least partially elastically surrounding the human being's chest or abdomen.

18. An apparatus to monitor two or more vital signs from a human being, the apparatus comprising:
two or more sensing circuit components, including at least two of the following:
at least two electrodes configured and arranged to sense an ECG signal from the human being,
at least two monochromatic LEDs and light sensors configured and arranged to sense one or more photoplethysmography (PPG) signals from the human being,
a temperature sensor, and
at least two electrodes configured and arranged to sense a thoracic impedance signal from the human being;
a signal acquisition, digitization, and computing module, including circuitry, configured and arranged to perform one or more of removing noise, extracting information useful for diagnosing a health or fitness characteristic of the human being, and compressing information to reduce data volume, via the two or more sensing circuit components, wherein the computing module is configured and arranged to increase the signal-to-noise ratio (SNR) of an input ECG signal by >15 dB while maintaining a quality of signal reconstruction (QSR) of >95%; and
a wireless communications circuit configured and arranged to transmit the two or more vital signs to a receiver.

19. A method for monitoring two or more vital signs from a human being, the method comprising:
performing two or more of the following:
sensing an ECG signal from the human being,
sensing, via two or more monochromatic LEDs and light sensors, one or more photoplethysmography (PPG) signals from the human being,
sensing temperature, and
sensing, via at least two electrodes, a thoracic impedance signal from the human being;
compressing information to reduce data volume to provide >7× compression while maintaining QSR of >95%, to produce data characterizing the two or more vital signs based on the sensing; and
wirelessly transmitting the data characterizing the two or more vital signs to a receiver.

20. The method of claim 19, further including performing one or more of removing noise and extracting information useful for diagnosing a health or fitness characteristic of the human being.

* * * * *